United States Patent [19]

Klingman

[11] 4,342,876

[45] Aug. 3, 1982

[54] METHOD FOR OXIDATION OF P-XYLENE AND METHOD FOR PREPARING DIMETHYLTEREPHTHALATE

[75] Inventor: Gilbert E. Klingman, Houston, Tex.

[73] Assignee: Bechtel International Corporation, San Francisco, Calif.

[21] Appl. No.: 219,184

[22] Filed: Dec. 22, 1980

[51] Int. Cl.³ ............ C07C 67/00; C07C 67/08; C07C 67/39; C07C 51/265

[52] U.S. Cl. .................... 560/77; 422/231; 562/412; 562/414; 562/415

[58] Field of Search ............... 560/77; 562/412, 414, 562/415

[56] References Cited

U.S. PATENT DOCUMENTS 3,923,867 12/1975 Baerns et al. .................... 560/77
4,032,563 6/1977 Harper et al. .................... 560/77

FOREIGN PATENT DOCUMENTS 2833585 12/1979 Fed. Rep. of Germany .
862391 3/1961 United Kingdom .

Primary Examiner—Natalie Trousof
Assistant Examiner—Vera C. Clarke
Attorney, Agent, or Firm—Townsend and Townsend

[57] ABSTRACT

A novel vertical induced circulation reactor is utilized to carry out the oxidation of p-xylene and p-methyltoluate with air in the presence of a catalyst to produce p-toluic acid and monomethylterephthalate (MMT). A novel method for preparation of dimethylterephthalate (DMT) is provided wherein the p-toluic acid and MMT formed according to the invention are esterified by conventional means in the presence of methanol to produce p-methyl toluate and dimethylterephthalate (DMT), respectively, the p-methyl toluate being recycled to the reactor as a reactant stream.

10 Claims, 3 Drawing Figures

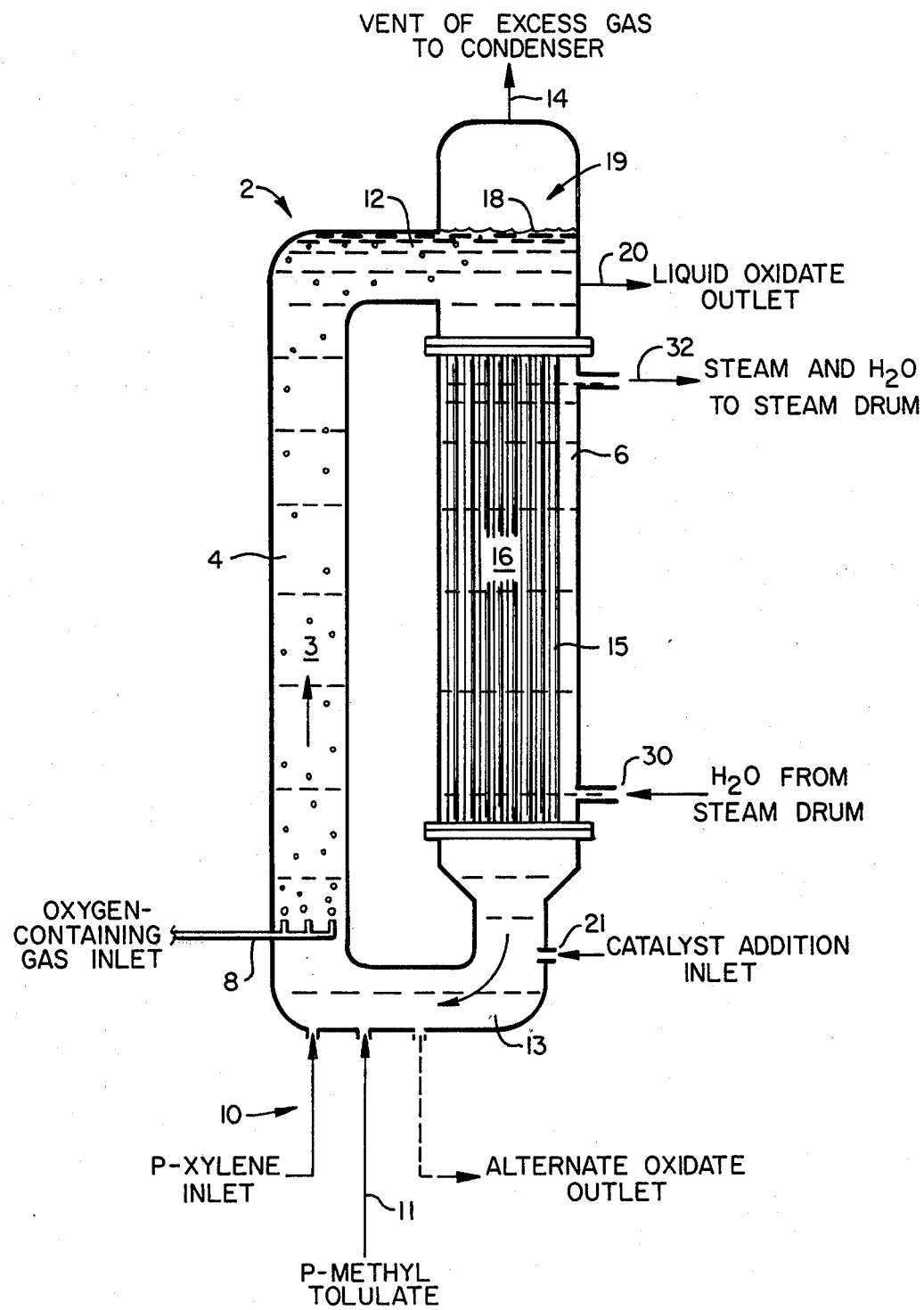
FIG._1.

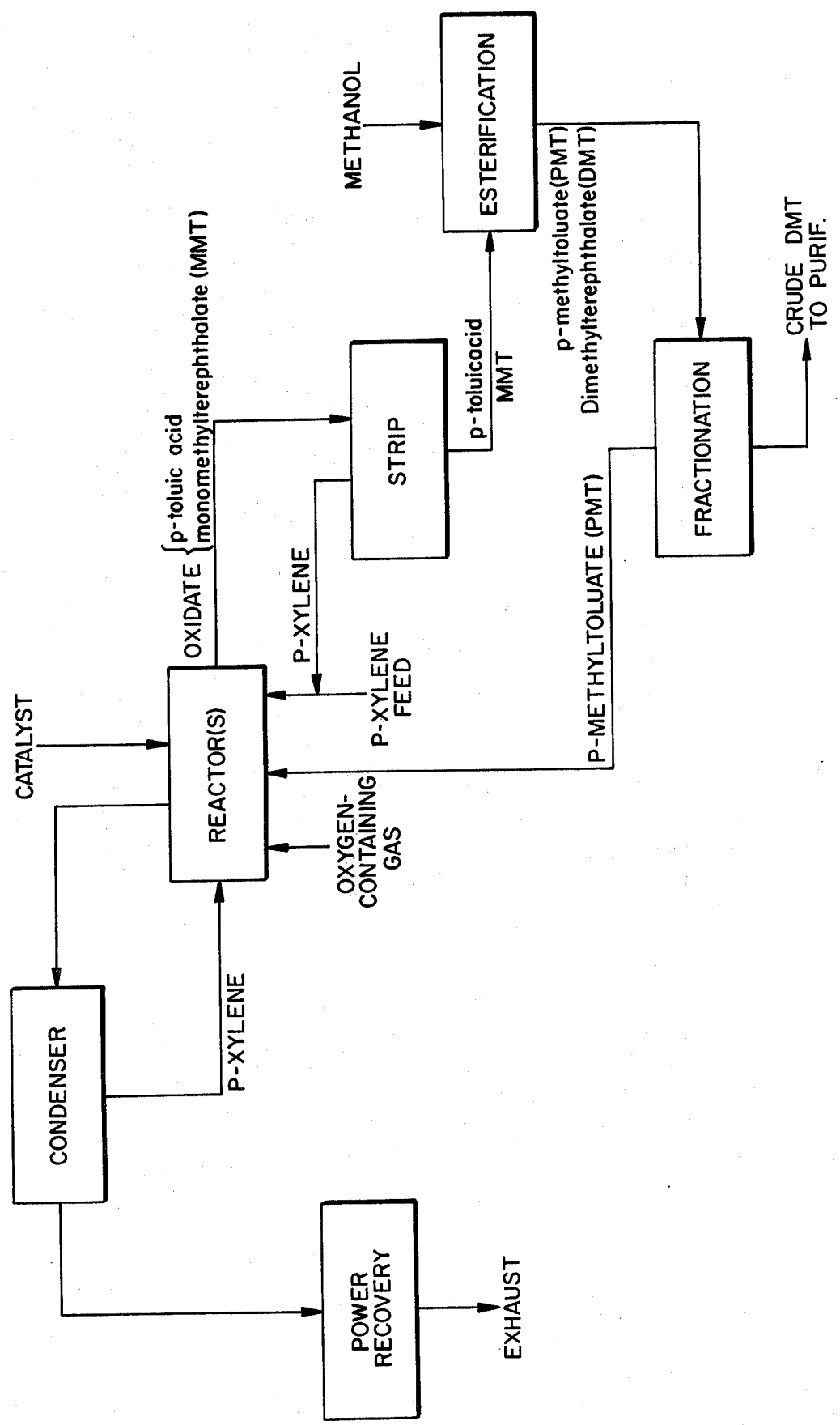
FIG._2.

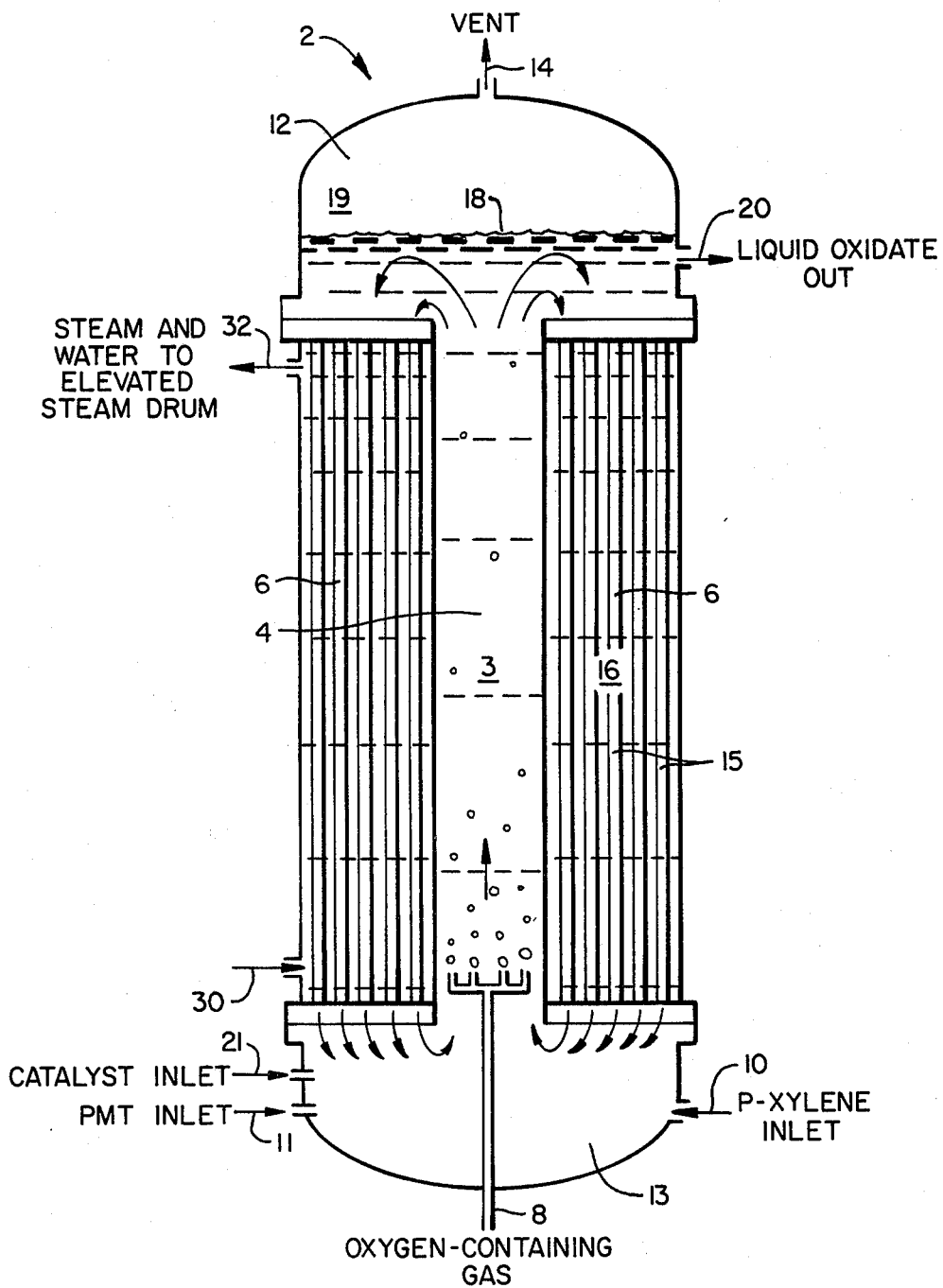
FIG._3.

METHOD FOR OXIDATION OF P-XYLENE AND METHOD FOR PREPARING DIMETHYLTEREPHTHALATE

BACKGROUND OF THE INVENTION

This invention relates to a method of and apparatus for oxidizing p-xylene, and in particular, to the use of an induced flow loop reactor for the oxidation of p-xylene and/or p-methyltoluate.

Various reaction sequences, methods, and apparatus for the oxidation of p-xylene, p-toluic acid, and esters thereof, to form terephthalates including dimethyl-terephthalate (DMT), are known. For example, U.S Pat. No. 4,185,073, teaches an apparatus for continuous production of terephthalic acid by catalytic air-oxidation of p-xylene in a benzoic acid-water liquid solvent system. U.S. Pat. No. 3,923,867, teaches a method of producing high purity monomethylterephthalate by oxidation of p-xylene. Various methods of producing terephthalic acid from p-xylene are taught in U.S. Pat. Nos. 3,513,193; 3,887,612; and 3,850,981.

The oxidation products of p-xylene have wide commercial and industrial application, particularly in the production of polyester fibers and films. Industrial-scale methods and apparatus for oxidation of p-xylene are known, but none to date achieve high yields and good temperature control utilizing relatively simple and inexpensive equipment.

Moreover, in each of the aforementioned patents, mechanical agitation means is utilized during oxidation. Not only do they require costly energy, i.e. utilities, to operate, but have the additional disadvantages of moving parts within the reactor, such as mechanical breakdowns. Other currently used oxidation reactors in which agitation is not provided suffer from significant temperature variations within the reactor and/or poor heat transfer characteristics, resulting in increased operating costs and lower product quality.

Reactors wherein circulation is induced without the need for an outside power source, e.g. electricity, or mechanical agitation are known. Liquid phase reactors, wherein the introduction of a gas to one part of the reactor induces circulation due to density differentiations, have been utilized for contacting liquid and solid particles. For example, U.S. Pat. No. 3,759,669, teaches a reactor with concentric reactor legs, in which introduction of gas maintains catalytic particles in suspension without the need of a circulating pump system. U.S. Pat. No. 3,552,934, uses a partition head with a plurality of channels to separate two such reactor legs or zones. U.S. Pat. No. 3,124,518 teaches a reactor configuration for hydrogenation, wherein the introduction of hydrogen induces the necessary circulation without mechanical agitation or stirring.

SUMMARY OF THE INVENTION

In accordance with the present invention, p-xylene is oxidized to p-toluic acid and/or p-methyltoluate is oxidized to monomethylterephthalate (MMT) at high circulation rates in an induced flow reactor loop without mechanical agitation or pumping. The circulation achieved by design of the reactor and the manner and amount of oxygen-containing gas-introduction into the reactor permits an essentially isothermal operation. Maximum temperature variation within the reactor can be limited to about 3°–5° F.

The oxidation of p-xylene and/or p-methyltoluate (PMT) can be effectively and efficiently carried out on a continuous basis as part of a continuous process for the production of DMT or other desirable end-products by utilizing an induced circulation reactor comprising two substantially vertical reactor columns or legs interconnected at their respective tops and bottoms by first and second interconnecting conduits or passages to form a "loop." According to the method of the present invention, oxidation of p-xylene and/or PMT is carried out in the presence of small amounts of catalysts in a reaction medium flowing through such a loop reactor by (a) introducing the liquid reactants, i.e. inputting p-xylene and/or PMT, into the loop through at least one liquid reactant inlet means; (b) introducing an oxygen-containing gas, such as air, into one of the two said reactor columns to gasify, i.e. reduce the density of, the reaction medium in this first reactor column through gas inlet means spaced below the top of said loop a vertical distance sufficient to cause circulation of the reaction medium through the loop, i.e. to cause the denser reaction medium in the other of said reactor columns to flow downward and the gasified, lighter reaction medium in said first reactor leg to flow upward; (c) inputting catalysts into the loop; (d) venting the excess gas from the top of the reactor loop to degasify, i.e. increase the density of, the reaction medium as it flows from said first reactor column to said second reactor column; and (e) cooling the reaction medium as it flows upward through the said first reactor column or downward through the second "downside" reactor column. The oxidate reaction products, i.e. p-toluic acid and/or monomethylterephthalate (MMT), are removed from the reactor, typically as overflow from the top of the reactor loop, at about the same rate of input as the liquid reactants.

More particularly, the reactor utilized in the method of the present invention operates as a liquid phase reactor with high liquid circulation rates without the need for mechanical agitation or pumping equipment. The motivating force for circulation is the difference in specific gravity or weight of the vertical interconnected reactor columns of the liquid reaction medium contained in the two legs of the reactor. One column contains a gas/liquid mixture while the other contains essentially ungasified liquid. The difference in specific gravity between the reaction medium in the first and second reactor columns is a result of the introduction of the oxygen-containing gas, such as air, to only the first or upside of the vertical reactor columns. The upside leg or column thus has a gasified section, whereas the other, i.e., the downside, reactor leg or column contains essentially only liquid reaction medium. Unreacted oxygen-containing gas and inerts are vented off the top of the loop, thereby effecting substantial removal of gases from the liquid reaction medium prior to its entering the downside leg. In the preferred embodiment, the non-gasified, or downside, portion of the loop, is in effect a tube and shell heat exchanger for removal of the heat of reaction. However, the tubular, i.e. the tube and shell, side can also be utilized as the gasified side, in which case it still functions to remove the heat of reaction, but then the flow is reversed and the liquid reaction medium flows up through the tubes as a result of the oxygen-containing gas being introduced through the gas inlet on the cooling or tubular side of the loop.

Significantly, by oxidizing p-xylene and/or PMT according to the method and apparatus of the present invention, the induced circulation through the reactor, including the heat exchange portion of the reactor, effected without mechanical agitation or stirring, is sufficient to maintain the point to point temperature variation in the reactor to less than 10° F. and often to within 3°–5° F. The excellent mixing achieved due to turbulent flow plus minimizing the temperature differential within the reactor results in high yields. Introduction of the gas in the appropriate amount and location results in adequate circulation, i.e. turbulent flow in the region of gas input plus a circulation through the heat exchanger sufficient to remove substantially all the heat of reaction and thus maintain a relatively constant temperature throughout the reactor and reaction medium.

BRIEF DESCRIPTION OF THE DRAWINGS

FIG. 1 is a cut-away partial front view of a reactor utilized for the oxidation of p-xylene and PMT in accordance with one embodiment of the present invention.

FIG. 2 is a schematic flow sheet drawing of a process for producing DMT wherein oxidation of p-xylene and/or PMT is carried out according to the present invention.

FIG. 3 is a cut-away front view of a reactor utilized for the oxidation of p-xylene in accordance with another embodiment of the present invention.

DETAILED DESCRIPTION OF THE INVENTION

FIG. 1 depicts one embodiment of a reactor useful for the oxidation of p-xylene and PMT, according to the present invention. The reactor 2 is an induced circulation "loop" reactor having first and second substantially vertical columns or legs, i.e. a first upside reactor column 4 and a second downside heat exchange column 6. The reactor columns 4 and 6 are interconnected at their tops and bottoms by connecting passages or conduits 12 and 13 to form a "loop." Liquid reactants, i.e. p-xylene and/or p-methyltoluate (PMT) and catalysts, are inputted to the reactor loop through p-xylene inlet means 10, PMT inlet means 11 and catalyst inlet means 21. Although the p-xylene inlet means 10 and the PMT inlet means 11 may be located anywhere in the loop, they are preferably not in the heat exchanger, and most preferably disposed upstream of the gas inlet means and near or about the bottom of the loop. Air or another oxygen-containing gas is inputted or introduced into said upside column 4 through gas inlet means 8, spaced from the top of the loop at a distance sufficient to induce the desired circulation, i.e. at least enough circulation through the heat exchange column 6 to permit the heat of reaction to be removed. Introducing gas into only one column of the loop gives the reaction medium in the reactor column 4 a lower density than that in the non-gasified column 6 thereby causing the reaction medium to circulate through the loop, upwardly in the first reactor column 4 and downwardly in the second reactor column 6. The excess gas and inerts are separated and exit the reactor through venting means 14 at the top of the loop, thereby allowing substantially degasified, and more dense, reaction medium to enter the downside column 6. Of course, by an appropriate relocation of the gas inlet the flow direction could be reversed to make column 6 the upside column and column 4 the downside column.

The downside column 6 is equipped with cooling means, such as the tube and shell heat exchanger 16 depicted in FIG. 1. In order to minimize the pressure drop through the reactor and to maintain the high circulation rate, the flow area of the heat exchanger 16 in the downside column 6 may be as large as or larger than the flow area, i.e. cross-sectional area, of the upside column 4.

The liquid-gas separation area 19 in the reactor 2 is typically but not necessarily above the downside column 6. In a reactor with a configuration such as that of FIG. 1, the liquid-gas interface 18 is preferably at about the same level as the top of the conduit or passage 12 interconnecting the tops of the reactor columns 4 and 6. The liquid oxidate comprising p-toluic acid and/or MMT can be removed from an oxidate outlet 20 disposed at about the same elevation as the top conduit 12 or alternatively about the bottom interconnecting conduit 13 as depicted in FIG. 1, but in either event should be on the down flow side of the reactor. The vertical distance between the interface 18 and the gas inlet means 8 is defined as the submergence level of the gas inlet 8. Typically the rate of circulation increases with submergence.

The consumption of oxygen during the oxidation reaction reduces the amount of gas reaching the top of the reactor loop. However, as will be known and understood by those skilled in the art, the circulation is not dependent upon gas reaching the top since the maintenance of any gasified section (height) will produce some degree of circulation. The taller the gasified section, i.e. the larger the submergence, the greater the circulation. A certain amount of the circulation rate can be attributed to the oxygen even though eventually much of it is consumed. The amount of inerts, such as nitrogen, present in the air feedstock will in any event create a high circulation rate within the reactor. The circulation rate through the heat exchanger will be sufficient to reduce the temperature variation within the reactor to about 5° F. When air is utilized as the oxygen-containing gas, the introduction of about 14.3 moles of air, i.e. about 3 moles of $O_2$, per mole of p-xylene and/or PMT to be oxidized results in more than adequate circulation and heat removal. The force causing circulation is balanced by the pressure drop through the reactor. By per mole p-xylene is meant per mole of p-xylene, PMT and/or any other intermediate of p-xylene which is itself oxidized. Typical reaction conditions are, temperature of about 140° C. to about 170° C. and pressure of about 4 to about 8 atmospheres.

The inherently low pressure drop through the reactor of the present invention is a direct result of its novel design. The wall effects (friction) on the flow of the reaction medium are minimal because of the relatively large diameters of the reactor columns. The height to diameter ratio of the reactor column which does not include the heat exchanger may be from 3:1 to 100:1 depending on reactor capacity and is typically in the range of from 5:1 to 10:1. The heat exchange tubes 15 will have diameters larger than those normally utilized in chemical reactors, i.e. having an outside diameter of 1 to 3 inches, more preferably about 2 inches O.D. The relatively large diameters of the tubes allow turbulent flow conditions to be maintained in the tubes with a resulting high heat transfer efficiency. The number of such tubes will be primarily dependent on the total cross-sectional or flow area desired. The length of the tubes is dependent upon heat transfer considerations, i.e. the length will be sufficient to effect enough heat removal to maintain the reaction medium temperature constant to within about 10° F. and preferably within about 3°–5° F.

In accordance with the present invention, the heat of reaction is removed by indirect heat exchange with another liquid and/or gas. The heat exchange surfaces are incorporated into the reactor in such a way as to permit a substantially unimpeded flow of the circulation rate of the reaction medium. In addition, consistent with the present invention, heat transfer surfaces may be inexpensively provided since the rapid circulation and turbulent flow allow the heat transfer to be effected utilizing high temperature (pressurized) water.

The sizing of the reactor for any particular design capacity is based upon calculations of heat transfer requirements for removal of the heat of reaction, gas velocity and throughput rate, and reaction kinetics. In calculating the surface area of the heat exchanger tubes, the overall heat transfer coefficient is the key parameter. Depending upon the manner in which the entire reactor is designed, the overall heat transfer coefficient may vary from 30 to 80 BTU/hr/ft$^2$/°F. Typically a coefficient of 50 to 60 BTU/hr/ft$^2$/°F. will be achieved if the flow areas are designed in accordance with the parameters set forth herein. Assuming the heat exchanger is located in the nongasified leg of the reactor, the gasified leg is sized so that the superficial gas velocity in that leg is between 0.25 and 4 feet per second and preferably between 1 and 1.5 feet per second. The cross sectional flow area so calculated is the minimum flow area provided in the nongasified leg. Thus if the heat exchanger is in the nongasified leg, the total of the inside cross sectional areas of all the heat transfer tubes provided should equal or exceed the cross sectional flow area of the other leg.

Often it is most economical to use heat exchanger tubes which are 20 feet in length, although this length is by no means a requirement. If more flow area is required than would be provided with the number of 20 foot long tube required for the heat transfer requirement, a larger number of shorter tubes are used. In this way both the flow area and heat transfer surface requirements are met.

Generally a reactor designed on the basis of flow area and heat transfer requirements will contain enough liquid volume so that reaction kinetic requirements are met. However, if additional volume is required it is simply and economically obtained by increasing the height of the wide diameter sections above or below the heat exchanger.

In the embodiment depicted in FIG. 1, water at a temperature of 270° to 338° F. and a pressure of 27 to 100 psig. will enter the shell of the downside reactor column 6 through water inlet 30 and will flow around the tubes 15 carrying the liquid reaction medium 3. Heat from the reaction medium will cause the pressurized water to form steam which exits the shell at steam outlet 32.

Where the desired process end-product is DMT (dimethylterephthalate) a mixture of p-xylene and p-methyltoluate is oxidized with air in the presence of heavy metal catalysts to produce p-toluic acid and MMT (monomethylterephthalate). No reaction solvent is necessary during oxidation, although the reaction may be carried out in acetic acid. The catalyst may be cobalt acetate or a mixture of cobalt and manganese acetates. The p-xylene and p-methyltoluate are continuously oxidized at 140° to 170° C. and 4 to 8 atmospheres pressure with air. A small amount of catalyst may be continuously added to the reactor so as to maintain a constant catalyst concentration. It will be understood that a small amount of catalyst is continuously withdrawn from the reactor with the overflowing oxidate. The catalyst is added as a solution in water or acetic acid.

A small amount of terephthalic acid may be formed due to the reaction of p-toluic acid with oxygen (air). Any terephthalic acid formed will be insoluble. However, the amount of terephthalic acid formed is very small due to the relative ease of oxidizing p-xylene and p-methyltoluate. Any terephthalic acid formed will be maintained in suspension and will overflow out of the reactor with p-methyltoluate and a small amount of unreacted p-xylene.

Referring to FIG. 2, the overflowing oxidate leaving the reactor is first steam stripped to remove p-xylene which can be recycled to the reactor. The remaining oxidate is then esterified with methanol by conventional methods, such as taught by U.S. Pat. No. 3,923,867. The crude ester obtained is subsequently fractionated, whereby p-methyltoluate is recovered overhead for recycle to the reactor. The bottom of the fractionation is separated in another column into crude DMT and residue. The DMT is further purified by crystallization or other known methods.

As will be known and understood by those skilled in the art, a number of induced flow reactors of the present invention may be operated in series, i.e. the oxidate product out of the first reactor may feed a second reactor, and if desired, the overflow of the second may feed a third reactor. The reactor operates continuously with feedstock constantly added and liquid oxidate continuously withdrawn. However, when first put into operation, unless there is a supply of p-methyltoluate with which to fill the reactor, it will typically be filled with p-xylene. In such a case no fresh p-xylene would be added until a sufficient concentration of p-methyltoluate has been formed downstream in the process for recycling to the reactor.

FIG. 3 depicts an alternative configuration of the loop reactor wherein the upside reactor column 4 is inside and concentric with the downside heat exchange column. The loop of the reactor of FIG. 3 is thus configured like a vertically elongated donut with the liquid reaction medium moving upward through the center of the donut and downward through the sides. The numerals utilized in FIG. 3 are the same as those in FIG. 1 for corresponding elements of the reactors.

It will be understood that the above description of the present invention is susceptible to various modifications, changes and adaptations, which are nevertheless within the scope of the invention and are intended to be understood as falling within the meaning and range of equivalents of the appended claims.

What is claimed is:

1. A method of oxidizing p-xylene to p-toluic acid and/or p-methyltoluate to monomethylterephthalate in a catalyst-containing reaction medium flowing through a loop reactor, said loop defined by first and second reactor columns and the interconnections of their respective tops and bottoms, comprising the steps of
   (a) inputting p-xylene and/or p-methyltoluate into said reactor loop through at least one liquid reactant inlet means;
   (b) introducing oxygen-containing gas into said first reactor column to gasify the reaction medium in said first reactor column through gas inlet means spaced from the top of said loop a vertical distance sufficient to cause reaction medium in said second reactor column to flow downwardly and gasified reaction medium in said first reactor column to flow upwardly;

(c) venting excess gas from the top of said reactor;

(d) cooling said reaction medium by cooling means disposed in one of said first and second reactor columns whereby said reaction medium flows through said cooling means; and (e) the oxidation being effected at a temperature of 140°–170° C. and a pressure of 4–8 atmospheres.

2. A method according to claim 1 wherein one of said reactor columns includes a heat exchanger having a flow area similar in size to the flow area of the other of said columns and said cooling comprises removing heat from said reaction medium at a rate sufficient to maintain the temperature variation of said reaction medium to within 10° F.

3. A method according to claim 1 wherein said oxygen-containing gas is air.

4. A method according to claim 1 wherein said first reactor column is inside and concentric with said second reactor column.

5. A method according to claim 1 wherein said step of inputting is on a continuous basis and further comprising the step of (e) removing said reaction medium containing p-toluic acid and/or monomethylterephthalate through oxidate outlet means at a rate which substantially maintains a constant liquid level in said reactor.

6. A method according to claim 5 wherein said p-toluic acid and/or monomethylterephthalate of step (e) is esterified to p-methyltoluate and/or dimethylterephthalate, and said p-methyltoluate is recycled to said reactor.

7. In a method of preparing dimethylterephthalate by catalytically oxidizing p-xylene and p-methyltoluate to form an oxidate comprising p-toluic acid and monomethylterephthalate and esterifying said oxidate to form dimethylterephthalate and p-methyltoluate, the improvement comprising:

(a) providing at least one induced flow loop reactor, each such reactor having first and second substantially vertical reactor legs interconnected to form a loop, at least one liquid reactant inlet means, at least one oxidate outlet means and at least one gas inlet means for introducing oxygen-containing gas into one of said first and second reactor legs, either of which said first and second reactor legs having cooling means;

(b) introducing said oxygen containing gas through said gas inlet means to partially gasify the reaction medium in the first reactor leg;

(c) venting gas from the top of said loop to substantially degasify said reaction medium as it flows from said first reactor leg to said second reactor leg;

(d) cooling said reaction medium as it flows through said reactor legs to remove the heat produced by said oxidation of p-xylene and p-methyltoluate;

(e) the temperature of the reaction medium being 140°–170° C.;

said gas inlet means being disposed in said first reactor leg at a vertical distance from the top of said loop such that said introducing causes the reaction medium in said second reactor leg to flow downward and gasified reaction medium in said first reactor leg to flow upward at a rate sufficient to maintain the temperature of the reaction medium within a variation of 10° F.

8. A method according to claim 7 wherein said p-methyltoluate formed from esterification of said oxidate is recirculated to said first reactor leg wherein the oxidation thereof takes place concurrently with the oxidizing of said p-xylene.

9. A method according to claim 7 wherein the temperature of the reaction medium is constant to within about 5° F.

10. A method according to claim 7 wherein said oxygen-containing gas is air.

* * * * *